(12) United States Patent
Dobbyn

(10) Patent No.: US 12,415,007 B2
(45) Date of Patent: *Sep. 16, 2025

(54) SYSTEM AND METHOD FOR PROBE CLEANING AND DISINFECTING

(71) Applicant: Gregory John Dobbyn, Creedmoor, NC (US)

(72) Inventor: Gregory John Dobbyn, Creedmoor, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/140,404

(22) Filed: Apr. 27, 2023

(65) Prior Publication Data

US 2023/0263922 A1  Aug. 24, 2023

Related U.S. Application Data

(63) Continuation of application No. 16/360,715, filed on Mar. 21, 2019, now Pat. No. 11,660,362, which is a
(Continued)

(51) Int. Cl.
*A61L 2/18* (2006.01)
*A61B 1/12* (2006.01)
(Continued)

(52) U.S. Cl.
CPC ............... *A61L 2/18* (2013.01); *A61B 1/123* (2013.01); *A61B 90/70* (2016.02); *A61L 2/24* (2013.01);
(Continued)

(58) Field of Classification Search
CPC .................. A61B 90/70; A61L 2/18
See application file for complete search history.

(56) References Cited

U.S. PATENT DOCUMENTS

| 4,763,678 A | 8/1988 | Ott |
| 5,425,815 A | 6/1995 | Parker et al. |

(Continued)

FOREIGN PATENT DOCUMENTS

JP  2004065612 A  3/2004

OTHER PUBLICATIONS

International Search Report and Written Opinion for International Patent Application No. PCT/US15/27124 completed pri Jun. 23, 2015.
(Continued)

*Primary Examiner* — Kevin Joyner
(74) *Attorney, Agent, or Firm* — Moore & Van Allen PLLC; Jeffrey R. Gray

(57) ABSTRACT

Embodiments of the invention are directed to apparatuses and methods for cleaning and disinfecting probes. A cleaner is utilized to remove foreign materials (e.g., bioburden, soil, and other like material) from the probe after it is removed from the patient by soaking and/or flushing the foreign materials from the probe. The cleaner may be an enzymatic detergent that has bacteriostatic properties to inhibit bacterial growth within the apparatus. The multiple enzymes in the cleaner attack the foreign material, and include low-foam properties for effective recirculation across cycles within the cleaning step. The probe is rinsed after the cleaning step, and after rinsing a disinfectant process is applied to the probe. The disinfectant soaks and/or flushes the probe for a specified amount of time across cycles of recirculation to disinfect the surface of the probe, and afterwards the probe is rinsed thoroughly to remove the disinfectant from the probe.

20 Claims, 6 Drawing Sheets

Related U.S. Application Data continuation of application No. 14/693,431, filed on Apr. 22, 2015, now Pat. No. 10,238,760.

(60) Provisional application No. 61/982,582, filed on Apr. 22, 2014.

(51) Int. Cl.
  *A61B 90/70* (2016.01)
  *A61L 2/24* (2006.01)
  *G01R 3/00* (2006.01)
  *B08B 3/04* (2006.01)
  *B08B 3/10* (2006.01)

(52) U.S. Cl.
  CPC .......... *G01R 3/00* (2013.01); *A61B 2090/701* (2016.02); *A61L 2202/17* (2013.01); *A61L 2202/24* (2013.01); *B08B 3/04* (2013.01); *B08B 3/10* (2013.01)

(56) References Cited

U.S. PATENT DOCUMENTS

| | | | |
|---|---|---|---|
| 6,132,691 A | 10/2000 | Coles | |
| 6,482,358 B1* | 11/2002 | Kelsch | A61L 2/18 422/292 |
| 6,558,620 B1* | 5/2003 | Sanford | A61B 1/123 134/102.2 |
| 7,641,873 B2 | 1/2010 | Coles et al. | |
| 8,506,900 B1 | 8/2013 | Ricciardi et al. | |
| 2002/0182105 A1 | 12/2002 | Nakanishi et al. | |
| 2003/0190256 A1 | 10/2003 | Halstead et al. | |
| 2004/0118291 A1* | 6/2004 | Carhuff | A47J 31/469 99/275 |
| 2005/0215906 A1 | 9/2005 | Coles et al. | |
| 2007/0185385 A1 | 8/2007 | Noguchi et al. | |
| 2010/0294322 A1 | 11/2010 | Wagemann et al. | |
| 2012/0020834 A1* | 1/2012 | Coles | A61L 2/186 422/292 |

OTHER PUBLICATIONS

Extended European Search Report for European Application No. 15782400.4 completed Dec. 12, 2017.

P. Kanagala et al: "Guidelines for transoesophageal echocardiographic probe cleaning and disinfection from the British Society of Echocardiography", European Journal of Echocardiography, vol. 12, No. 10, Oct. 1, 2011 (Oct. 1, 2011), pp. i17-i23, XP055684510, GB ISSN: 1525-2167, DOI: 10.1093/ejechocard/jer095.

Office Action for European Application No. 15782400.4 dated May 11, 2020.

Examination Search Report dated May 13, 2021 for Canadian Application No. 2,946,744.

Examination Search Report dated Dec. 17, 2021 for Canadian Application No. 2,946,744.

Examination Search Report dated Oct. 14, 2022 for Canadian Application No. 2,946,744.

Examination Search Report dated Apr. 28, 2023 for Canadian Application No. 2,946,744.

* cited by examiner

SYSTEM AND METHOD FOR PROBE CLEANING AND DISINFECTING

RELATED APPLICATIONS AND PRIORITY CLAIM

This application is a continuation of, and claims priority to U.S. patent application Ser. No. 16/360,715 entitled "System and Method for Probe Cleaning and Disinfecting", filed on Mar. 21, 2019, which is a continuation of, and claims priority to U.S. patent application Ser. No. 14/693,431 entitled "System and Method for Probe Cleaning and Disinfecting," filed on Apr. 22, 2015, which issued into U.S. Pat. No. 10,238,760 on Mar. 26, 2019, which claims priority to Provisional Application No. 61/982,582 entitled "System and Method for Probe Cleaning and Disinfecting" filed Apr. 22, 2014, all of which are hereby expressly incorporated by reference herein.

FIELD

This application relates generally to the field of cleaning and disinfecting probes, and more particularly to apparatuses and methods for providing a process for both cleaning and disinfecting the probes.

BACKGROUND

Some probes, and in particular Transesophageal Echocardiograph (TEE) probes, which are channel-less ultrasound transducer probes that are inserted down the esophagus of a patient, cannot undergo sterilization and do not contact sterile areas of the human body. Since these probes cannot be sterilized using traditional methods, high-level disinfection of these types of probes is required.

BRIEF SUMMARY

Embodiments of the invention are directed to apparatuses and methods for disinfecting probes, and in particular TEE probes, by providing a cleaning process before submitting the probe to the disinfecting process. As such, a cleaner is first utilized to remove foreign material (e.g., bioburden, soil, and the like) from the probe after the probe is removed from the patient by soaking and/or flushing the probe with the cleaner. The cleaner may be a detergent or a detergent with one or more enzymes to enhance cleaning. The multiple enzymes in the cleaner rapidly attack soils, and include low foam properties for effective recirculation for various cycles of cleaning the probe. The probe is rinsed after the cleaning step to remove the residual cleaner from the probe and from within the fluid circuit. After rinsing a high-level disinfection process is applied to the probe. The high-level disinfectant soaks and/or flushes the probe for a specified amount of time, and afterward, the probe is thoroughly rinsed again to remove the disinfectant from the probe and from within the fluid circuit.

One embodiment of the invention comprises an apparatus for cleaning and disinfecting a probe. The apparatus comprises a probe reservoir assembly, wherein the probe reservoir assembly is configured for securing a probe for the cleaning and the disinfecting. The apparatus further comprises a cleaner assembly operatively coupled to the probe reservoir assembly, wherein the cleaner assembly is configured for providing a cleaner to the probe reservoir assembly for the cleaning of the probe before the disinfecting. The apparatus further comprises a disinfectant assembly operatively coupled to the probe reservoir assembly, wherein the disinfectant assembly is configured for providing a disinfectant for the disinfecting of the probe after the cleaning.

In further accord with an embodiment of the invention, the probe reservoir assembly comprises a probe reservoir configured for securing at least a portion of the probe.

In another embodiment the invention further comprises a probe tube operatively coupled to the probe reservoir assembly and configured for securing at least a portion of the probe for the cleaning and the disinfecting.

In yet another embodiment of the invention, the cleaner assembly comprises a cleaning reservoir configured for storing the cleaner; and a cleaning dispenser configured for delivering the cleaner directly or indirectly to the probe reservoir assembly.

In still another embodiment the invention further comprises a water filter assembly operatively coupled to the probe reservoir assembly and the cleaner assembly; and wherein the water filter assembly comprises a water filter housing and a water filter for filtering water used in the apparatus.

In further accord with an embodiment of the invention, the apparatus further comprises a heater assembly comprising a heater configured for heating the water, the cleaner, and the disinfectant.

In another embodiment of the invention, the cleaner from the cleaner assembly and the water from the water filter assembly are mixed to create a cleaning solution that is used for cleaning the probe.

In yet another embodiment, the invention further comprises a disinfectant reservoir configured for receiving a single use disinfectant container with the disinfectant. The single use disinfectant container may be a ready to use dose, or the single use disinfectant container may be a concentrated dose that is configured for mixing with the water to create a disinfectant solution, either of which may be used for disinfecting the probe.

Another embodiment of the invention comprises an apparatus for cleaning and disinfecting a probe. The apparatus comprises a probe reservoir assembly comprising a probe reservoir, wherein the probe reservoir assembly is configured for securing at least a portion of the probe for the cleaning and the disinfecting. The apparatus further comprises a probe tube operatively coupled to the probe reservoir, wherein the probe tube is configured for securing at least another portion of the probe within the probe tube for the cleaning and the disinfecting. The apparatus further comprises a cleaner assembly comprising a cleaner reservoir configured for storing a cleaner, and a cleaner dispenser configured for dispensing the cleaner, wherein the cleaner assembly is operatively coupled to the probe reservoir assembly, wherein the cleaner assembly is configured for providing the cleaner to the probe for the cleaning before the disinfecting. The apparatus also comprises a disinfectant assembly comprising a disinfecting reservoir configured for storing a single use disinfecting container with a disinfectant, wherein the disinfectant assembly is operatively coupled to the probe reservoir assembly, and wherein the disinfectant assembly is configured for providing the disinfectant to the probe for the disinfecting the probe after the cleaning.

In further accord with an embodiment of the invention, the invention further comprises a water filter assembly comprising a water housing and a water filter configured to filter the water received from a water inlet. The water is mixed with the cleaner for creating a cleaner solution for the cleaning of the probe. The single use disinfectant container may be a ready to use dose of the disinfectant, or the single use disinfectant container may be a concentrated dose of the disinfectant that is configured for mixing with the water to create a disinfectant solution, for the disinfecting of the probe.

In another embodiment the invention further comprises a heater assembly comprising a heater. The heater assembly is operatively coupled to the cleaner assembly, the disinfectant assembly, and the water supply assembly. The heater is configured to heat the cleaner solution, the disinfectant solution, or the water.

Another embodiment of the invention comprises a method for cleaning and disinfecting a probe. The method comprises inserting the probe into a probe reservoir assembly, wherein the probe reservoir assembly is configured for securing at least a portion of the probe for the cleaning and the disinfecting. The method further comprises cleaning the probe before the disinfecting by applying a cleaner to the probe through the use of a cleaner assembly operatively coupled to the probe reservoir assembly. The method also comprises disinfecting the probe by applying a disinfectant to the probe through the use of a disinfectant assembly operatively coupled to the probe reservoir assembly.

In further accord with an embodiment of the invention, the probe reservoir assembly comprises a probe reservoir configured for securing at least a portion of the probe.

In another embodiment of the invention, inserting the probe into the probe reservoir assembly further comprises inserting at least a portion of the probe into a probe tube that is operatively coupled to the probe reservoir assembly.

In yet another embodiment of the invention, the cleaning the probe comprises storing the cleaner in a cleaning reservoir of the cleaner assembly, and delivering the cleaner to the probe reservoir assembly directly or indirectly using a cleaning dispenser of the cleaner assembly.

In still another embodiment the invention further comprises filtering water using a water filter assembly comprising a water filter housing and a water filter. The water is received from a water inlet. The water filter assembly is operatively coupled to the probe reservoir assembly and the cleaner assembly.

In further accord with an embodiment of the invention, the invention further comprises heating the water using a heater assembly comprising a heater.

In another embodiment the invention further comprises mixing the cleaner from the cleaner assembly and the water from the water filter assembly to create a cleaning solution that is used for the cleaning of the probe.

In still another embodiment the invention, the disinfectant assembly comprises a disinfectant reservoir configured for receiving a single use disinfectant container with the disinfectant. The single use disinfectant container may be a ready to use dose, or a concentrated dose that is configured for mixing with the water to create a disinfectant solution, each of which may be used for disinfecting the probe.

To the accomplishment the foregoing and the related ends, the one or more embodiments comprise the features hereinafter described and particularly pointed out in the claims. The following description and the annexed drawings set forth certain illustrative features of the one or more embodiments. These features are indicative, however, of but a few of the various ways in which the principles of various embodiments may be employed, and this description is intended to include all such embodiments and their equivalents.

BRIEF DESCRIPTION OF THE DRAWINGS

Figure 1:
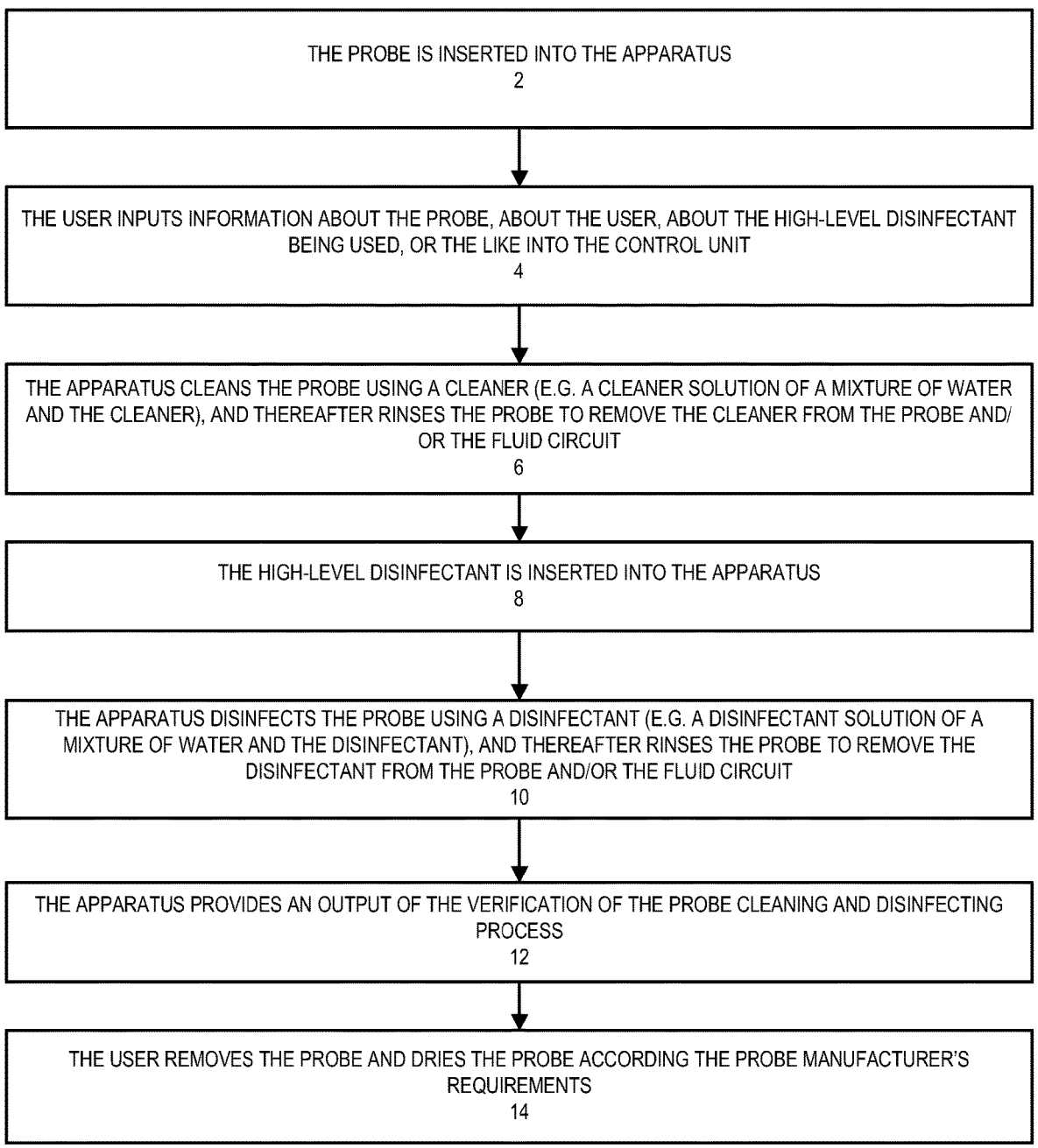
Figure 2:
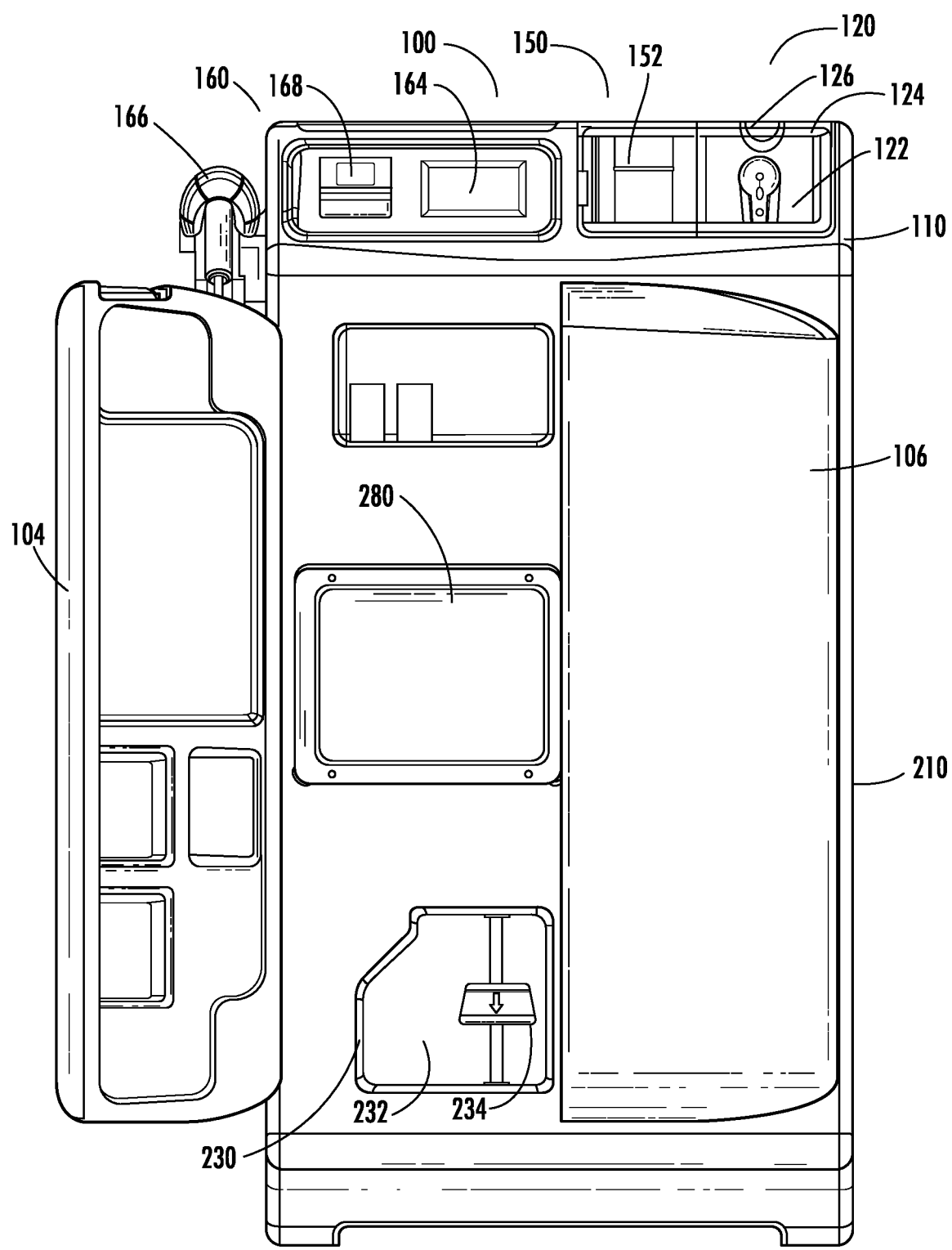
Figure 3:
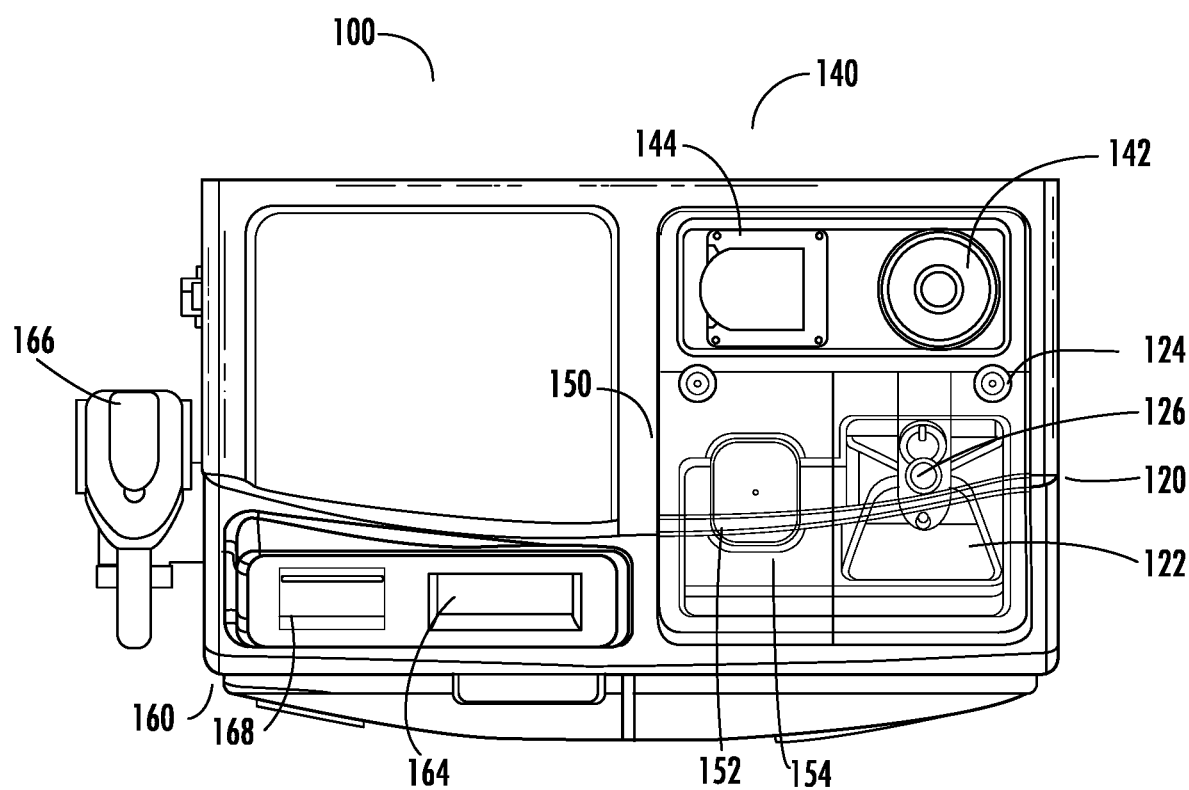
Figure 4:
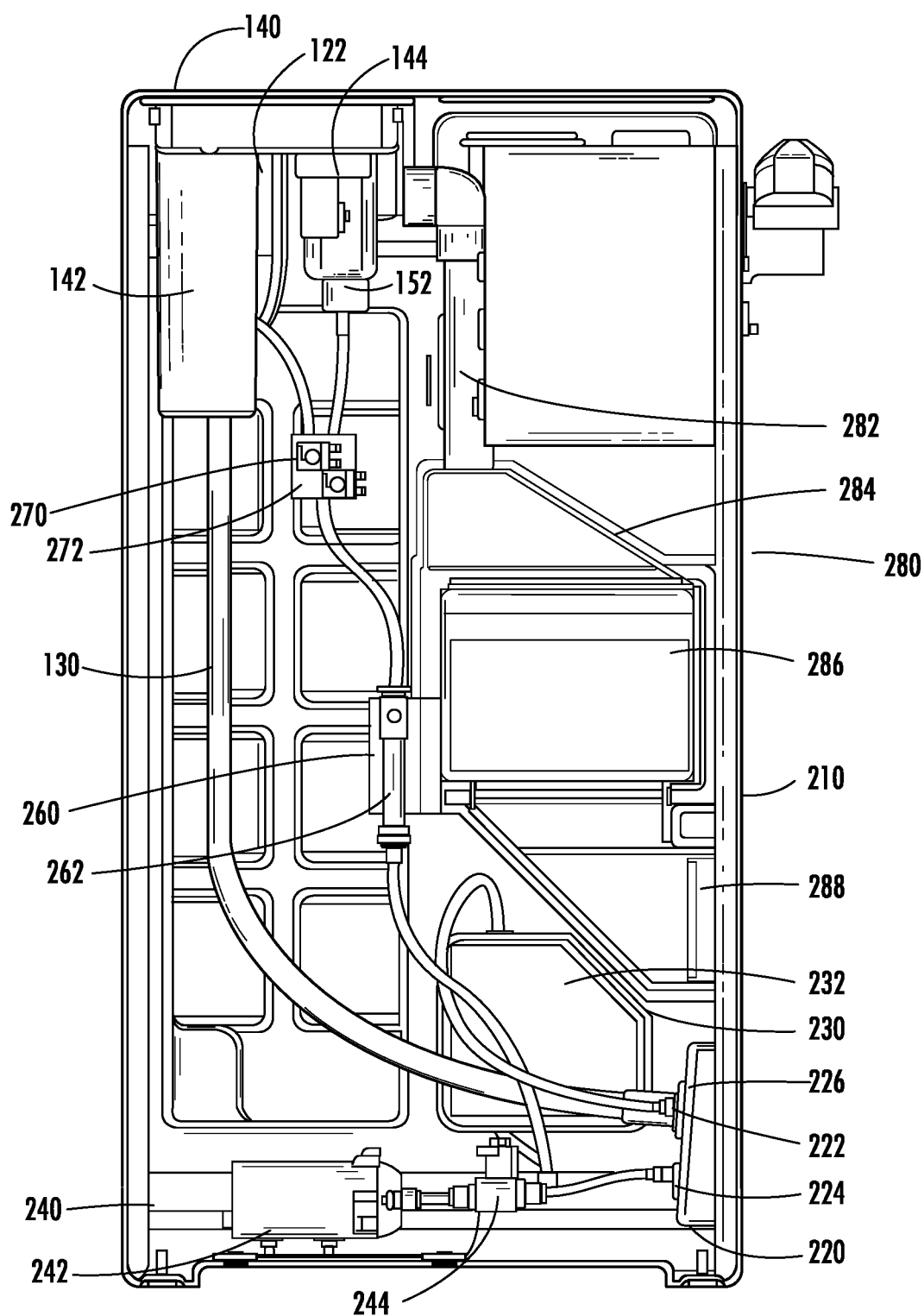
Figure 5:
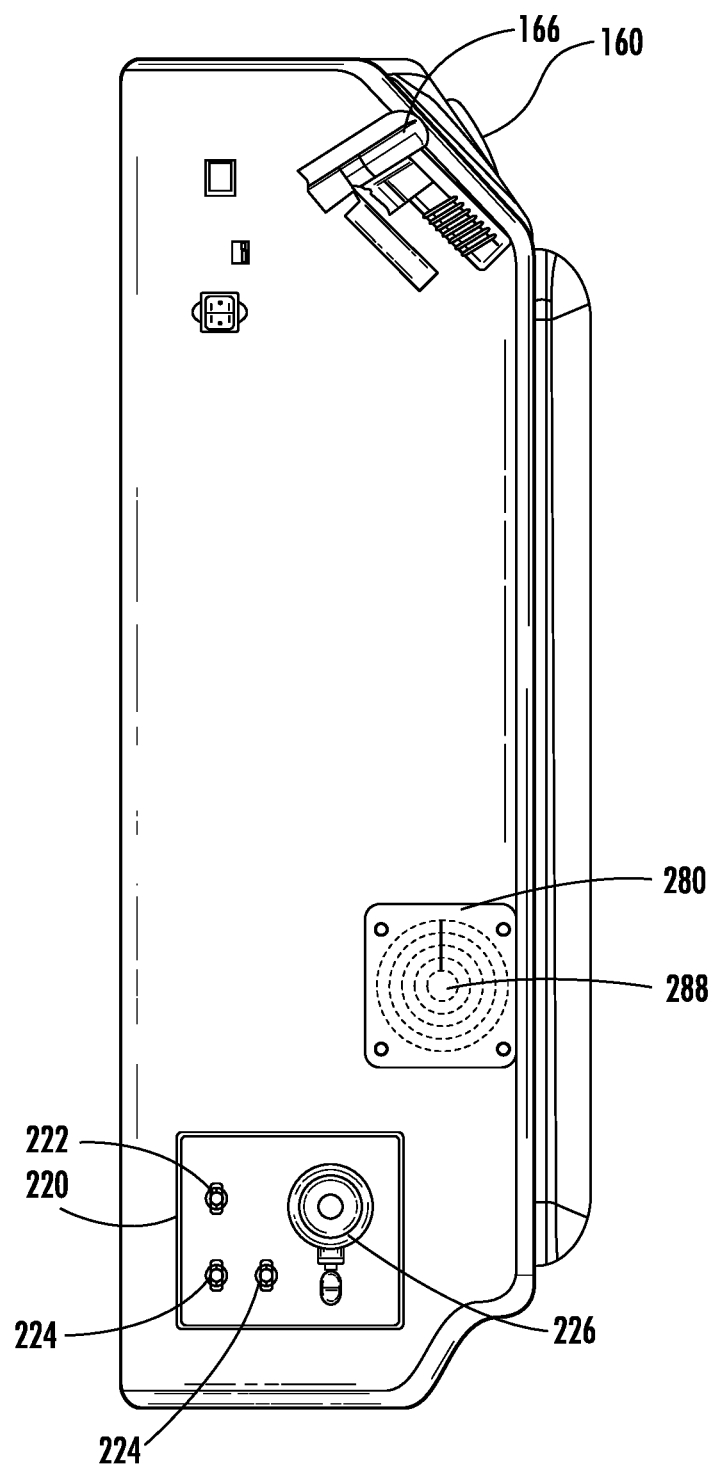
Figure 6:
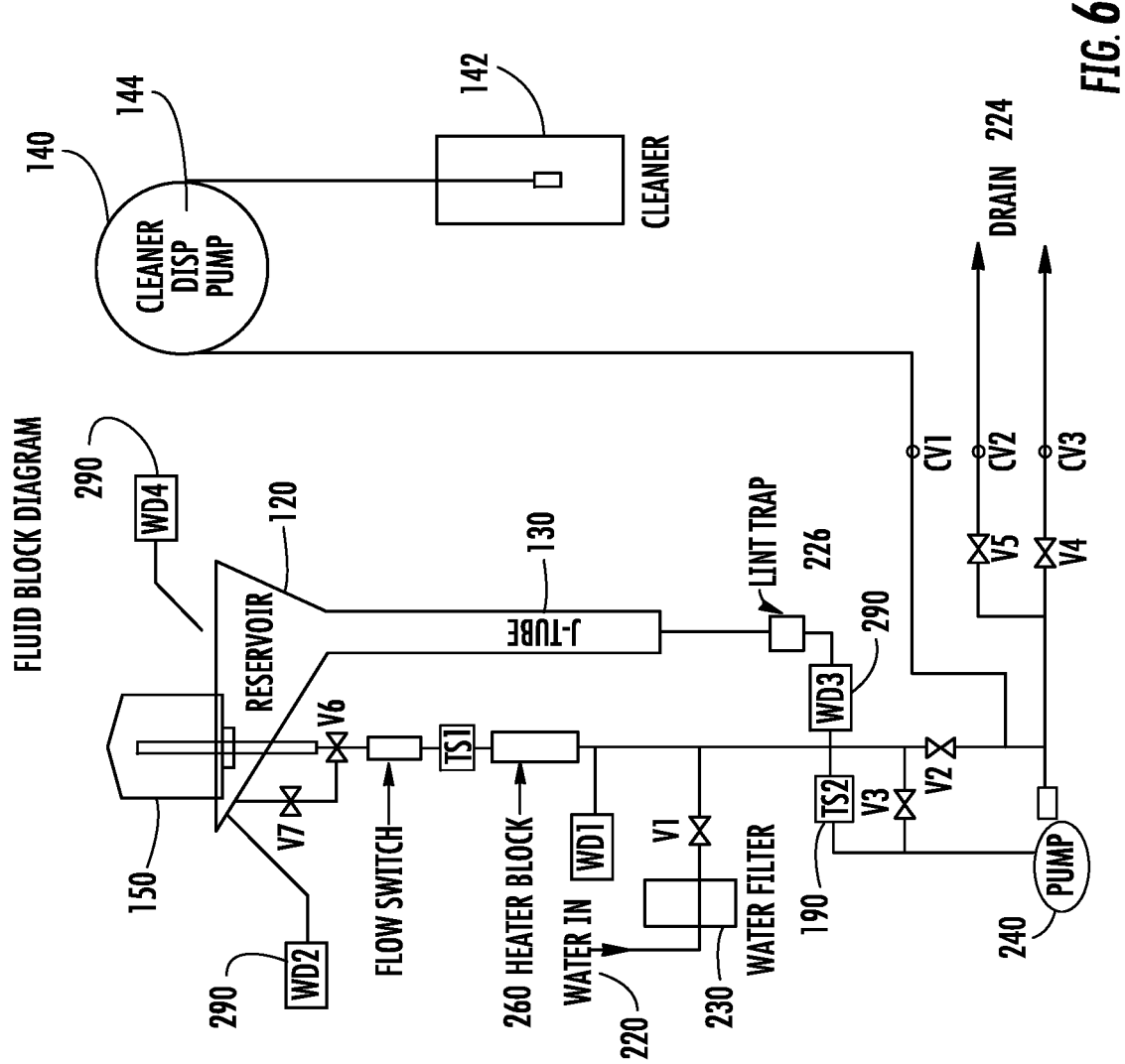

Having thus described embodiments of the invention in general terms, reference will now be made to the accompanying drawings, where:

FIG. 1 illustrates a high level process flow for the automatic cleaning and disinfecting of probes, in accordance with embodiments of the invention;

FIG. 2 illustrates a front view of the cleaning and disinfecting apparatus, in accordance with embodiments of the invention;

FIG. 3 illustrates a top view of the cleaning and disinfecting apparatus, in accordance with one embodiment of the invention;

FIG. 4 illustrates a rear view of the cleaning and disinfecting apparatus with the housing removed, in accordance with embodiments of the invention;

FIG. 5 illustrates a side view of the cleaning and disinfecting apparatus, in accordance with embodiments of the invention; and FIG. 6 illustrates a schematic diagram of the fluid flow within the cleaning and disinfecting apparatus, in accordance with embodiments of the invention.

DETAILED DESCRIPTION OF EMBODIMENTS OF THE INVENTION

Embodiments of the present invention now may be described more fully hereinafter with reference to the accompanying drawings, in which some, but not all, embodiments of the invention are shown. Indeed, the invention may be embodied in many different forms and should not be construed as limited to the embodiments set forth herein; rather, these embodiments are provided so that this disclosure may satisfy applicable legal requirements. Like numbers refer to like elements throughout.

The apparatuses and methods of the present invention are described specifically with respect to cleaning and disinfecting TEE probes; however, it should be understood that the apparatuses and methods of the present invention may be utilized on other types of probes. The apparatuses and methods described herein utilize a cleaner to soak and/or flush the probes to remove bioburden, soil, and the like (e.g., hemoglobin, carbohydrates, proteins, endotoxin, or the like) (described collectively herein as "foreign material") from the probe after it is removed from a patient. The cleaner may be an enzymatic detergent that has bacteriostatic properties to inhibit bacterial growth in the apparatus 100 (e.g., within the cleaner assembly 140, supply lines, fluid circuit, or the like). The multiple enzymes in the cleaner rapidly attack soils, and have low foam properties for effective recirculation within the apparatus 100. The probe is rinsed after cleaning to remove or substantially remove the residual cleaner from the probe and the rest of the fluid circuit. After rinsing a high-level disinfectant process is applied to the probe. The high-level disinfectant soaks and/or flushes the probe for a specified amount of time to disinfect the surface of the probe, and thereafter the probe is thoroughly rinsed to remove or substantially remove any remaining disinfectant from the probe or from within the rest of the fluid circuit. The patient never interacts with the apparatus 100, as such the apparatus 100 provides a layer of insulation between the patient and the cleaner and the disinfectant through both physical barriers as well as the air filter assembly 280, which is described in further detail later.

The term cleaner used herein may describe the cleaner in its form before it is mixed with water to form the cleaner solution, and/or the cleaner solution. It should be understood that the use of the term cleaner may be substituted with the term cleaner solution throughout this application, and as such this specification may describe that the cleaner itself and/or the cleaner solution (e.g., the cleaner mixed with water) may be utilized within the process steps or within the components of the apparatus 100 described herein. Likewise, the term disinfectant used herein may describe the disinfectant in its form before it is mixed with water to form the disinfectant solution, and/or the disinfectant solution. It should be understood that the use of the term disinfectant may be substituted with the term disinfectant solution throughout this application, and as such this specification may describe that the disinfectant itself and/or the disinfectant solution (e.g., the disinfectant mixed with water) may be utilized within the process steps or within the components of the apparatus 100 described herein. Moreover, it should be understood that the term fluid circuit described herein may include the components and tubes within the apparatus in which the cleaner, disinfectant, and/or the water passes through.

The present invention provides for the cleaning and disinfecting of a probe within the apparatus 100. The apparatus 100 comprises a housing 102 that at least partially encloses the components of the apparatus 100, which both securely hold the probe to avoid damage to the probe and also control the processes for directing the cleaner and the disinfectant through the flow paths of the apparatus 100 to clean and disinfect the probe.

FIG. 1 illustrates a high level process flow for cleaning and disinfecting a TEE probe. As illustrated by block 2 a single soiled TEE probe is inserted into the apparatus 100. As will be discussed in further detail later, the probe is secured safely within a probe reservoir assembly 120 and/or the probe tube 130. In other embodiments of the invention, the apparatus 100 may be able to accommodate multiple probes at a time, for example within one or more probe reservoir assemblies 120 and/or probe tubes 130.

As illustrated by block 4, a user inputs information into the apparatus 100 through a control unit assembly 160, which is described in further detail later. The information may be related to the probe being cleaned and disinfected, the user operating the apparatus 100, the cleaner and/or the high-level disinfectant being used to clean or disinfect the probe, the duration of time and/or temperatures for cleaning, rinsing, disinfecting, and final rinsing, or other process steps. In some embodiments, these programmed times for cleaning, rinsing, disinfecting, final rinsing, and/or other like process steps are pre-programmed into the apparatus 100. As such, in some embodiments when the processing temperatures and/or times are pre-programed, the user does not have the ability to change these inputs. If the pre-programed process is not followed or the cycle is interrupted before completion, the cycle may be aborted and a failure notice may be provided to the user (e.g., failure ticket is printed, displayed on an interface, or the like). After the inputs are set, the user may begin the cleaning, rising, disinfecting, and final rinsing steps of the process.

Block 6 of FIG. 2 illustrates that the apparatus 100 cleans the probe by applying a pre-determined amount of cleaner to the probe from the cleaner assembly 140, as will be discussed in further detail later. The cleaner may be supplied as a dose from a multi-use supply (e.g., 50 or more or less doses within a container, or other like dose amount), or as a dose from a single use supply (e.g., single use container). In some embodiments of the invention the single use container and/or the dosage from a multi-use container may be utilized without the need to add additional water (e.g., a ready to use dose), while in other embodiments the single use container and/or the dosage from a multi-use container (e.g., a concentrated dose) may be mixed with water to form a cleaner solution, in order to disinfect the probe. In some embodiments the cleaner is mixed with filtered water from the water filter assembly 230 to create the cleaner solution before being used to clean the probe. Moreover, in some embodiments the cleaner is heated to approximately 40 degrees C. In other embodiments the cleaner is heated to a temperature in the range of 35 degrees C. to 45 degrees C., inclusive. However, it should be understood that the temperature to which the cleaner is heated may be within this range, overlap this range, or fall outside of this range in alternate embodiments of the invention. As explained in further detail later the cleaner may be heated before it is mixed with the water, after it is mixed with the water, or the water may be heated before it is mixed with the cleaner.

The cleaner (e.g., the heated cleaner solution) is delivered to the probe, and thereafter recirculated back through the fluid circuit to the probe again in one or more cleaner cycles to clean the probe before the probe is disinfected. As explained in further detail below a heater system 260 may continuously heat the cleaner, as it is recycled through the fluid circuit in order to maintain the temperature of the cleaner at the desired temperature range. In some embodiments of the invention, the cleaner may remain stagnant for a period of time to allow the probe to soak within the cleaner. In some embodiments of the invention, the cleaner may be applied to the probe (e.g., delivered and recirculated) for a minimum of five (5) minutes to remove the foreign material from the surface of the probe. In other embodiments, the cleaner may be applied to the probe for less than or greater than five (5) minutes. Each use of the cleaner may be a single use, and thus, the cleaner waste is discarded to the one or more drains 224 after a cleaning cycle. In one embodiment the cleaner may have a dedicated cleaner drain to keep the cleaner waste from mixing with the disinfecting waste, which is described in further detail later. Moreover, in some embodiments a lint filter may be used to remove the foreign material from the cleaner (e.g., cleaner solution) during each cycle of the cleaner through the fluid circuit or after the cleaning step is complete. In some embodiments, the cleaner may be delivered to the probe and discharged from the apparatus in one or more cycles (e.g., a single cycle), and thereafter, a new second cleaner (e.g., the heated cleaner solution) may be delivered to the probe in a second cycle, and so on (e.g. third cleaner delivered in a third cycle, or the like).

After cleaning, the probe, as well as the components and tubes of the fluid circuit, are thoroughly rinsed by water from the water filter assembly 230 and/or the water inlet 222, in one or more cleaner rinsing cycles. In some embodiments, after each cleaner rinsing cycle or after the cleaner rinsing step, the cleaner rinsing waste is also discarded to the one or more drains 224, such as the dedicated cleaner drain. The water used to rinse the probe may also be heated in some embodiments of the invention (e.g., to the same or similar temperatures as described with respect to the cleaner and/or the disinfectant described below). During the cleaner rinsing step the water may be recycled through the fluid circuit, or new water may be used within each cycle of the cleaner rinsing step.

As illustrated by block 8 of FIG. 1, a predetermined amount of high-level disinfectant is loaded into the apparatus 100. For example, in some embodiments of the invention the high-level disinfectant is a single use container (e.g., bottle, package, or the like) that is utilized once and the container is disposed of after the disinfecting step is completed. The single use container may be punctured inside of the apparatus 100 to contain and minimize splashes, spills, and vapors within the apparatus 100. In other embodiments of the invention, the disinfectant may be delivered from a disinfectant supply that has more than a single use, and that is already loaded into the apparatus 100. In some embodiments of the invention the single use container and/or the dosage from a multi-use container may be utilized without the need to add additional water (e.g., a ready to use dose), while in other embodiments the single use container and/or the dosage from a multi-use container (e.g., a concentrated dose) may be mixed with water to form a disinfectant solution that is used to disinfect the probe.

Block 10 of FIG. 1 illustrates that the apparatus 100 heats the high-level disinfectant (e.g., the disinfectant solution) to approximately 38-40 degrees C., inclusive, before being delivered to the probe for disinfecting. In some embodiments the disinfectant may be heated utilizing the heater assembly 260. The disinfectant may be heated before being combined with the water, after being combined with the water, or the water may be heated before being combined with the disinfectant. In some embodiments the temperature may be within, outside, or overlapping the recited temperature range of the disinfectant (e.g., disinfectant solution).

In some embodiments of the invention, the disinfectant (e.g., disinfectant solution) may be delivered to the probe and recirculated back through the system to the probe in one or more disinfectant cycles to disinfect the probe. In some embodiments of the invention, the disinfectant may remain stagnant for a period of time to allow the probe to soak within the disinfectant. The disinfectant may be heated each time it is recirculated through the fluid circuit in order to maintain the temperature of the disinfectant to the desired temperature range. In some embodiments, the disinfectant may comprise Glutaraldehyde, and make up 2.65% of the disinfectant solution, with the remainder comprising of water and/or other components. In other embodiments of the invention a different type of disinfectant may be utilized and/or the amount of the disinfectant element may be below or above the recited 2.65%. The disinfectant may be applied (e.g., delivered and recycled) to the probe for at least five (5) minutes at the desired temperature range. In other embodiments of the invention the minimum amount of soaking and/or flushing time may be below or above the at least five (5) minutes. In one embodiment, after disinfecting the probe the disinfectant (e.g., disinfectant solution) may have a dedicated disinfectant drain in order to keep the disinfectant waste from mixing with the cleaner waste, which is described in further detail later. In some embodiments, the disinfectant may be delivered to the probe and discharged from the apparatus in a one or more cycles (e.g., a single cycle), and thereafter, a new second disinfectant (e.g, the heated disinfectant solution) may be delivered to the probe in a second cycle, and so on (e.g. third disinfectant delivered in a third cycle, or the like). The disinfectant waste may be required to be kept separate from the cleaner waste (and other rinsing water waste) because the disinfectant waste may have to be chemically inactivated, depending on the requirements of different facilities or areas of use.

Thereafter, the water (e.g., heated water) thoroughly rinses the disinfectant off the probe, as well as out of the components and tubes of the fluid circuit, in one or more disinfectant rinsing cycles. In some embodiments, after each disinfectant rinsing cycle or after the disinfectant rinsing step, the disinfectant rinsing waste is also discarded to the one or more drains 224, such as the dedicated disinfectant drain. The water used to rinse the probe may also be heated in some embodiments of the invention (e.g., to the same or similar temperatures as described with respect to the disinfectant and/or cleaner). During the disinfectant rinsing step the water may be recycled through the fluid circuit, or new water may be used within each cycle of the disinfectant rinsing step.

As was the case with the cleaner step, in some embodiments a lint filter may be used to remove the foreign material from the disinfectant (e.g., disinfectant solution) or rinsing water during each cycle of the disinfectant or rinsing water, or after the disinfectant step or rinsing steps are complete.

The water used herein for creating a cleaner solution, a disinfectant solution, or for rinsing may be 0.2-micron filtered bacteria free water. In other embodiments of the invention the water used to create the cleaner solution, the disinfectant solution, or for rinsing the probe may be water that is less than or greater than the 0.2 micron filtered bacteria free water.

In some embodiments of the present invention, since the disinfectant used with each cycle is received from a single use disinfectant container, no monitoring of the disinfectant's potency is required, nor is there any requirement for daily testing of the disinfectant. The single use containers are created with the desired potency, and as such no measurement of the disinfectant solution is needed before it is utilized for disinfection.

Block 12 of FIG. 1 illustrates that the apparatus 100 may provide output of the verification of the cleaning and disinfecting of the probe. The verification of the cleaning and disinfecting of the probe may be based on the use of sensors that measure temperature (e.g., temperature sensors 190), wet/dry areas of the apparatus 100 (e.g., wet/dry sensors 290), or other like process or apparatus parameters, which are described in further detail later. For example, the apparatus 100 may provide the results of diagnostic tests that confirm that the probe has been properly disinfected because the probe was cleaned, rinsed, disinfected, and rinsed again with solutions for the desired durations and at the desired temperatures. The output verification may occur in the form of a printed document. However, in other embodiments of the invention, the output may be displayed on a screen that is operatively coupled to the apparatus 100 (e.g., within the apparatus 100 or on a computer display operatively coupled to the apparatus 100). In other embodiments of the invention, the output may be e-mailed, texted, instant messaged, or transferred through any other electronic means in order to provide the output to the desired user.

After the rinsing process in block 10, and after, before, or during the output verification process of block 12, the probe is removed from the apparatus and dried according to the probe manufacturer's instructions, as illustrated by block 14 in FIG. 1. After drying, the apparatus 100 is ready for a new cycle immediately after the preceding cycle is completed. A single cycle (e.g., from insertion of a probe to the removal of the probe after cleaning and disinfecting) may take approximately 25 minutes. It should be understood that in other embodiments of the invention the cycle may be less than 25 minutes or greater than 25 minutes.

FIGS. 2-5 illustrate various views of the apparatus 100 in accordance with one embodiment of the present invention. The apparatus 100 may comprise a head assembly 110 and a base assembly 210, as illustrated in FIGS. 2-4. The base assembly 210 holds and provides support for the internal components of the apparatus 100, while the head assembly 110 houses and supports the probe (e.g., when inserted into the apparatus 100), the disinfectant, the cleaner, and some of the components required to complete the cleaning and disinfecting processes. It should be understood that in some embodiments, the apparatus 100 may be configured in a single housing assembly that is a combination of the head assembly 110 and the base assembly 210, and will work in the same or similar way as is described herein. Moreover, it should also be understood that the head assembly 110 and the base assembly 210 may be split into two or more additional assemblies and work in the same or similar way as is described herein. It should also be understood that the assemblies and individual components thereof, which are described as being located in the head assembly 110 may in fact be located in the base assembly 210 and vice versa, and moreover, these assemblies and components thereof will still operate in the same or similar manner as described herein.

In one embodiment, the head assembly 110 comprises a probe reservoir assembly 120, as illustrated in FIGS. 2 and 3. The probe reservoir assembly 120 may comprise a probe reservoir 122 and a probe reservoir cover 124. The probe reservoir cover 124 comprises a probe cover aperture 126 for receiving a probe with a first portion (e.g., the portion that is or may be inserted into the body of a patient) and a second portion (e.g., the portion that includes the handle, electrical connection, and/or cord of the probe). The probe reservoir 122 may be operatively coupled to a probe tube 130 (e.g., a j-tube, or the like) that is operatively coupled to the water inlet and drain assembly 220 located in the base assembly 210. In some embodiments of the invention, the probe tube 130 may be a part of the probe reservoir assembly 120. The probe tube secures the first portion of the probe by housing the probe within the probe tube 130 to prevent the probe from being damaged during the cleaning, rinsing, disinfecting, and final rinsing processes. As such, the first portion of the probe may be completely secured within the probe tube 130; however, in some embodiments at least a portion of the first portion of the probe may be secured within the probe reservoir 122 of the probe reservoir assembly 120. The second portion of the probe (e.g., the handle, electrical connection, and/or cord of the probe) may be secured within the probe reservoir 122 and/or probe reservoir cover 124. In some embodiments of the invention only the first portion of the probe is cleaned and disinfected in the probe reservoir assembly 120 (e.g., within the probe reservoir 122) and/or within the probe tube 130 coupled to the probe reservoir assembly 120. The second portion of the probe (e.g., the handle, chord, electrical connection, or the like) may sit outside of the probe reservoir assembly 120 (e.g., probe reservoir 122) and may be cleaned and disinfected by the user before or after the cleaning and disinfecting process is applied to the first portion of the probe. The second portion of the probe may be damaged if it is submerged in the solutions and water that are used within the apparatus 100 for cleaning, disinfecting, and rinsing the first portion of the probe.

The first portion of the probe (e.g., within the probe reservoir 122 and/or within the probe tube 130) is thoroughly cleaned, rinsed, disinfected, and finally rinsed in order to allow the probe to be reused on subsequent patients. It should be understood that in other embodiments of the invention the probe reservoir assembly 120 may be combined with other assemblies, split into one or more multiple assemblies, or configured in other ways in order to provide a means for securing the probe, and in particular the first portion of the probe, for cleaning and disinfecting, while preventing the second portion of the probe from being subjected to potentially damaging conditions (e.g., being submerged in cleaning solutions, disinfecting solutions, or water). In other embodiments there may be multiple probe reservoirs assemblies 120, or multiple probes may be fit within the probe reservoir assembly 120, in order to clean multiple probes at once.

The head assembly 110 may further comprise a cleaner assembly 140, as illustrated in FIGS. 3 and 4. The cleaner assembly 140 comprises a cleaner reservoir 142 and a cleaner dispenser 144 (e.g., a cleaner pump, or other like means for distributing the cleaner solution). The cleaner assembly 140 is operatively coupled to the fluid circuit. For example, the cleaner assembly 140 may deliver the cleaner directly or indirectly to the tubing of the fluid circuit, to the probe reservoir assembly 120, to the probe tube 130, to the water filter assembly 230, to the main pump assembly 240, and/or to the heater assembly 250. As previously discussed the cleaner may be mixed with the water in the fluid circuit, heated, delivered to the probe, and recycled through the system one or more times. The cleaner (e.g., cleaner solution) is used to remove the foreign material from the probe before it is disinfected using the disinfectant. The cleaner removes material from the surface of the probe to allow the disinfectant in the process step described below to disinfect the surface of the probe that may contain residual foreign material that cannot be seen by the naked eye.

The head assembly 110 may further comprise a disinfectant assembly 150, as illustrated in FIGS. 2-4. The disinfectant assembly 150 may comprise a disinfectant reservoir 152, a disinfectant cover 154, and a means for puncturing (e.g., projection, punch, blade, scissor, or the like) a disinfectant container containing the disinfectant. The disinfectant reservoir 152 is configured for receiving the disinfectant container (e.g., a one-time use bottle or package), which provides the disinfectant for mixing with the water, and for delivery to the probe assembly 120 (e.g., probe reservoir 122) for disinfecting the probe. The disinfectant (e.g., disinfectant solution) is utilized to remove, kill, or otherwise sterilize the external surfaces of the probe that may have residual foreign material (e.g., residual bioburden, soil, and other like biological material) that is left on the surface of the probe after the initial cleaning process.

It should be understood that in other embodiments of the invention the cleaner assembly 140 and the disinfectant assembly 150, may be embodied in a single assembly, combined with other assemblies, split into two or more multiple assemblies, or configured in other ways in order to clean and disinfect the probe.

As illustrated in FIG. 2, the head assembly 110 may further comprise a control unit assembly 160 for housing the electronic components of the apparatus 100. The control unit assembly 160 may comprise a user interface 162 that is utilized to control the apparatus 100 and the electrical components for running the user interface 162. In some embodiments the user interface 162 may comprise a touchscreen 164 and/or keypad, a scanner 166 (e.g., barcode scanner, QR code scanner, digital image scanner, or other like scanner), and an output device 168 (e.g., printer, output interface, connection to computer system, touchscreen 164, or the like). The touchscreen 164 and/or the keypad enable the user to initiate operation of the unit. The scanner 166 allows the user to input data to the apparatus 100, for example data related to the cleaner, disinfectant, probe, user, process durations and/or temperatures, or the like, as previously discussed with respect to FIG. 1. The output device 168, such as the printer, provides the user with a diagnostic output of the machine condition, operating status, success or failure of the cleaning and disinfecting of the probe, and/or the process parameters (e.g., temperatures, wet/dry conditions, durations of the steps of the process, or the like) of the cleaning and disinfecting process. For example, the output may include the temperatures from the temperature sensors 190, wet/dry indications from the wet/dry sensors 290, a filter replacement notification, duration of the cleaning, rinsing, disinfecting, and/or final rinsing process steps, or the like. It should be understood that in other embodiments of the present invention the control unit assembly 160 may be combined with other assemblies, separated into two or more other assemblies, or configured in other ways in order to allow the user to control the apparatus 100 and receive output regarding the cleaning and disinfecting of the probe.

The body assembly 210 may comprise a water inlet and drain assembly 220, as illustrated in FIGS. 4 and 5. The water inlet and drain assembly 220 may comprise a water inlet 222, one or more drains 224, and a lint trap 226, which may all be operatively coupled to the housing 102 of the base assembly 210. The water inlet 222 provides a location to receive water and provide the water to the water filter assembly 230, which is discussed in further detail below. The drains 224 allow for the removal of used cleaner waste, disinfectant waste, and/or rinse water waste (e.g., cleaner rinsing waste or disinfecting rinsing waste) that are flushed through the system, and specifically through the probe tube 130 that operatively couples the probe reservoir 122 and the water inlet and drain assembly 220. The one or more drains 224 may include a specific drain for disinfectant waste and disinfecting rinsing waste, and a specific drain for cleaner waste and cleaner rinsing waste. The lint trap 226 is used to catch and separate the foreign material (e.g., bioburden, soil, and other biological material) from and the cleaner, disinfectant, and/or water (e.g., cleaner waste, disinfectant waste, cleaner rinsing waste, disinfecting rinsing waste, or the like) received from the probe reservoir 122 and the probe tube 130 as the probe is cleaned, rinsed, disinfected, and final rinsed. For example, the lint trap 226 may be used to remove the foreign material from the cleaner, disinfectant, and/or water as they are recycled through the fluid circuit or as they are drained out of the system after completion of the cleaning, rinsing (e.g., cleaner rinsing), disinfecting, or final rinsing (e.g., disinfecting rinsing) steps. The lint trap may be emptied as necessary, and the used cleaner waste, disinfectant waste, and/or water waste may be disposed of or recycled as needed. It should be understood that in other embodiments of the present invention the water inlet and drain assembly 220 may be combined with other assemblies, separated into two or more other assemblies, or configured in other ways in other embodiments of the invention in order to provide the source of water to the apparatus 100 and to remove the waste products of cleaning, rinsing, disinfecting, and final rinsing from the apparatus 100. In one embodiment the water inlet and drain assembly 220 (or another assembly) may be operatively coupled to (e.g., contain, be connected to, or the like) a water supply tank that houses at least a portion of the water for use as the water supply for mixing with the cleaner or disinfectant, and/or used as the rinse water. In still other embodiments, one or more waste tanks may be operatively coupled to the drain assembly 220 (or another assembly). The one or more waste tanks may be utilized to hold the waste from the cleaner and/or cleaner rinse cycles, and/or the disinfectant and/or disinfectant rinse cycles. The waste may be held within the one or more waste tanks while the waste material is inactivated to protect the public waste system. This embodiment may be particularly useful for the disinfectant and/or disinfectant rinse water, which may be required to be inactivated before disposing of the waste.

The body assembly 210 further comprises a water filter assembly 230, as illustrated in FIG. 4. The water filter assembly 230 may comprise a water filter housing 232, a water filter 234, and water tubes and valves that receive water from the water inlet and drain assembly 220 and delivers the water directly or indirectly to the probe reservoir assembly 120, or other assemblies as discussed herein. The water filter 234, as previously discussed may be a 0.2 micron water filter that filters water from particles that are greater than 0.2 microns. In other embodiments of the invention the water filter may be configured to filter particles that are less than or greater than 0.2 microns. In some embodiments, when the water filter 234 requires replacement, the apparatus 100 may undergo pasteurization at temperatures of approximately 70-75 Celsius for approximately thirty (30) minutes in order to flush out the apparatus 100 and ensure that the water filter 234 is operating properly before the apparatus is used for further cleaning and disinfecting. In other embodiments of the invention the temperature of pasteurization may be inside, outside, or overlapping this temperature range and/or the duration may be above or below thirty (30) minutes of pasteurization. It should be understood that in other embodiments of the present invention the water filter assembly 230 may be combined with other assemblies, separated into two or more other assemblies, or configured in other ways in order to supply the water for mixing with the cleaner to create the cleaner solution, for mixing with the disinfectant to create the disinfectant solution, or for rinsing the probe and/or the fluid circuit before and after cleaning and/or disinfecting.

As illustrated in FIG. 4, the body assembly 210 may further comprise a main pump assembly 240 that is used to pump water from the water filter assembly 230 and/or the water inlet 222 to the probe reservoir assembly 120 as needed to clean, disinfect, and rinse the probe and/or the fluid circuit. The main pump assembly 240 may also be utilized to pump at least some of the cleaner or disinfectant to the probe reservoir assembly 120 along with the water. The main pump assembly 240 may comprise a pump 242 and a pump manifold 244. The pump manifold 244 is utilized to operatively couple the pump 242 to the water filter assembly 230, as well as directly or indirectly to the water inlet and drain assembly 220, the heater assembly 260, the disinfectant valve assembly 270, the probe reservoir assembly 120, the probe tube 130, the cleaner assembly 140, and/or the disinfectant assembly 150. It should be understood that in other embodiments of the present invention, the main pump assembly 240 may be combined with other assemblies, separated into one or more other assemblies, or configured in other ways in order to pump the water, cleaner, or disinfectant needed for cleaning, disinfecting, and rinsing, to the probe reservoir assembly 120.

The body assembly 210 may further comprise a heater assembly 260, as illustrated in FIG. 4. The heater assembly 260 may comprises a heater 262 and tubes and valves for heating and supplying the heated water and heated solutions described herein to the probe reservoir assembly 120, the probe tube 130, and to recycle the water and solution described herein throughout the fluid circuit and back to the probe reservoir assembly 120 and/or the probe tube 130. The heater assembly 260 may be operatively coupled to the probe reservoir assembly 120, the probe tube 130, the cleaner assembly 140, the disinfectant assembly 150, the water filter assembly 230, and/or other assemblies described herein. In some embodiment, the heater assembly 260 may be located between the disinfectant valve assembly 270 (discussed below) and the main pump assembly 240.

The heater 262, in some embodiments may heat the mixture of the water and the cleaner (e.g., cleaner solution), or the mixture of the water and the disinfectant (e.g., disinfectant solution) after the solutions are created. In other embodiments the heater 262 may heat the water before the water is mixed with the cleaner or disinfectant, or when the water is applied to the probe reservoir assembly 120 or probe tube 130 by itself for rinsing. In still other embodiments of the invention the heater 262 may heat the cleaner and/or the disinfectant before they are mixed with the water. The water and/or the solutions are heated to the desired temperatures discussed herein by the heater 262 before being delivered to the probe assembly 120 or probe tube 130 to clean, disinfect, or rinse the probe. It should be understood that in other embodiments of the present invention, the heater assembly 260 may be combined with other assemblies, separated into one or more other assemblies, or configured in other ways in order to heat the water and/or the cleaner and disinfectant, for cleaning, disinfecting, and rinsing the probe in the probe reservoir assembly 120 or the probe tube 130.

A disinfectant valve assembly 270 may also be included in the body assembly 210, as illustrated in FIG. 4. The disinfectant valve assembly 270 may comprise a disinfectant valve 272 and supply tubes that receive the disinfectant from the disinfectant assembly 140 and the water from the main pump assembly 240, and deliver the mixture of water and disinfectant (e.g., the disinfectant solution) to the probe reservoir assembly 120. It should be understood that in other embodiments of the present invention the disinfectant valve assembly 270 may be combined with other assemblies, separated into two or more other assemblies, or configured in other ways in order to mix the water and disinfectant together and to supply the disinfectant solution to the probe reservoir assembly 120 and/or the probe tube 130.

The body assembly 210 may further comprise an air filter assembly 280, as illustrated in FIGS. 4 and 5. The air filter assembly 280 may comprise an air filter duct 282, an air filter housing 284, an air filter 286, and a fan 288. The fan 288 may pull any fumes from the cleaner, and more particularly from the disinfectant, away from the user located near the apparatus 100, and especially near the insertion point of the probe in the probe reservoir assembly 120. As such, the air filter duct 282 may be operatively coupled to the probe assembly reservoir 120, the probe tube 130, the cleaner assembly 140, the disinfectant assembly 150, and/or generally within the housing of the apparatus 100. The air filter duct 282 may be operatively coupled to the fan 288, for example through the air filter housing 284 and/or the air filter 286, in order to draw the fumes into the air filter housing 282 through the air filter 286 to remove or reduce potentially dangerous components from the fumes, and to exhaust the air out of the apparatus 100 through the fan 282. In one embodiment the air filter 286 is a carbon air filter that absorbs the glutaraldehyde in the fumes of the disinfectant. However, in other embodiments of the invention the air filter 286 may be any type of filter that removes or reduces potentially dangerous components from the fumes of the cleaner and/or the disinfectant. It should be understood that in other embodiments of the present invention, the air filter assembly 280 may be combined with other assemblies, separated into one or more other assemblies, or configured in other ways in order to remove fumes from the apparatus 100. It should be understood that the air filter 286 may comprise an RFID tag, or other indication illustrating the type of filter that may be used to remove the fumes form the cleaner and/or disinfectant. In other embodiments of the invention detector sensors may be utilized to indicate when the filter 286 has reached, or is about to reach, its end of useful life. The detector sensors may be operatively coupled to the control unit assembly 160, and thus, the user may be notified when the filter 286 has reached, or is about to reach, its end of useful life.

The housing 102 of the apparatus may comprise various features to access the components of the apparatus. In one embodiment the housing 102 may include a housing door 104 that may be utilized to access the air filter assembly 280 for accessing and replacing the air filter 286, and to access the water filter assembly 230 for accessing and replacing the water filter 234. In another embodiment the housing 102 may include a housing service panel 106 that allows a user to access the one or more assemblies contained within the housing 102.

As generally discussed with respect the various assemblies described herein, each assembly that transfers water, cleaner, disinfectant, a mixture of these fluids, or the like may utilize supply and return lines (e.g., tubing) to operatively couple the assemblies together and to transfer the fluids from one assembly to another. As previously discussed the assemblies and the supply and return lines may be described herein as the fluid circuit. The supply and return lines may be as illustrated in part in FIG. 4, and further illustrated in one embodiment of the invention, in the schematic diagram of FIG. 6, which is discussed in further detail below.

As illustrated by FIG. 6, the probe is inserted in the probe reservoir assembly 120 and the probe tube 130, and the cleaner is dispersed (e.g., through the cleaner pump 144) into the supply lines for the eventual delivery of the cleaner to the probe reservoir assembly 120. The cleaner mixes with the water (e.g. from the water inlet and drain assembly 220 or the water filter assembly 230) to form the cleaner solution. The main pump assembly 240 pumps the cleaner solution to the heater assembly 260 in order to heat the cleaning solution to the desired temperature, and thereafter the main pump assembly 240 pumps the heated cleaning solution into the probe reservoir assembly 120. The cleaning solution fills the probe reservoir 122 and/or the probe tube 130 to clean the first section of the probe (e.g., portion inserted into the patient). In some embodiments, as illustrated in FIG. 6 the main pump assembly 240 recycles the cleaning solution from the probe reservoir 122 and/or the probe tube 130 back to the heater 260 to keep the cleaning solution at the desired temperature range, and eventually back to the probe reservoir 122 and/or the probe tube 130 for further cleaning in a continuous loop for the desired amount of cleaning time. The cleaning solution clears the foreign material (e.g., bioburden, soil, and other like biological material) from the surface of the probe by soaking and/or flushing the cleaning solution through the probe reservoir assembly 120 and/or the probe tube 130 in one or more cycles. The lint trap 226 may filter the foreign material out of the cleaning solution during each of the one or more cycles or after the cleaning step is completed. After cleaning the recycling of the cleaner solution is shut off, and the cleaner solution drained out of the apparatus through the one or more drains 224 (e.g., the dedicated cleaner drain). Thereafter, the main pump assembly 240 may then pump water (e.g., heated water) from the water inlet and drain assembly 220 and/or the water filter assembly 230 into the probe reservoir assembly 120 and/or the probe tube 130 to thoroughly rinse the cleaner solution off of the probe. The cleaning rinse water waste may also be drained out of the apparatus through the one or more drains 224 (e.g., the dedicated cleaner drain).

The user may then insert an unopened single use disinfectant container into the disinfectant reservoir 152 of the disinfectant assembly 150. The single use disinfectant container may be inserted at the beginning of the process, or in some embodiments may be inserted after the cleaning process is completed. Inserting the disinfectant container after the cleaning process may prevent the disinfectant from mixing with cleaning solution in the probe reservoir assembly 120 during the cleaning operation. In some embodiments of the invention the disinfectant may be TD-5, which is used by other systems for disinfecting medical instruments. The dosage of the disinfectant within the container may be pre-determined in order to remove the need to test the disinfectant in a reservoir before each disinfecting step in order to identify if the disinfectant has the desired potency. However, in other embodiments of the invention the container of disinfectant may be a multi-use bottle that the disinfectant assembly 150 may regulate in order to apply the desired amount to the probe assembly 120. As illustrated in FIG. 6 the water is heated first and then mixed with the disinfectant to create the disinfectant solution before being distributed to the probe reservoir assembly 120 and/or the probe tube 130. The main pump assembly 240 recycles the disinfectant solution from the probe reservoir assembly 120 and/or the probe tube 130 to the heater assembly 260 to maintain the desired temperature range of the disinfectant solution before being delivered back to the probe reservoir assembly 120 and/or the probe tube 130. The disinfectant solution soaks and/or flushes the probe and the fluid circuit for at least five (5) minutes. In other embodiments the disinfectant is mixed with water before the heater assembly 240 heats the disinfectant solution, and before the disinfectant is first delivered to the probe reservoir assembly 120 and/or the probe tube 130.

After the disinfecting step, the probe is then thoroughly rinsed using the water (e.g., heated or unheated) for 10-12 minutes, to remove the disinfectant solution from the probe. In other embodiments of the invention the probe may be rinsed within a duration range that is inside of this range, outside of this range, or overlaps this range. A previously discussed the probe is removed from the apparatus 100 and dried according to the manufacture's specifications.

FIG. 6 also illustrates a number of valves at various locations that are utilized to open and close the fluid circuit to deliver or cut off the supply of water, cleaner, disinfectant, cleaner solution, disinfectant solution, cleaner solution waste, disinfectant waste, cleaner rinse water waste, and/or disinfectant rinse water waste to the various components of the apparatus, as described herein and as illustrated in FIG. 6. For example, in one embodiment of the invention the V1 valve is utilized for turning on/off the water supply to the system; the V2 valve is used to allow the fluid (e.g., cleaner, disinfectant, rinse water, or the like) from circulating continuously through the fluid circuit; the V3 valve may be used for permitting the fluid under pressure exiting the probe tube 130 an easier avenue of escape; the V4 valve may be used to drain the cleaner and/or cleaner rinse water; the V5 valve may be used to drain the disinfectant and/or the disinfectant rinse water; the V6 valve may be used to release the disinfectant into the fluid circuit; and the V7 valve may be utilized to release the cleaner, disinfectant, and/or rinse water into the reservoir 120.

Moreover, as illustrated by FIG. 6, check valves may be utilized to control the flow of the fluid in the fluid circuit; for example, the CV1 check valve may prevent fluid in the fluid circuit from entering the cleaner pump and/or cleaner reservoir 142. The CV2 and CV2 check valves may be used to prevent waste exiting the drain lines from returning back to the fluid circuit.

Software monitors the cleaning and disinfecting process using temperature sensors 190 and wet/dry sensors 290. As illustrated by the schematic diagram in FIG. 6, temperature sensors 190 may be located in, or at the exit of, the heater assembly 260 and after the probe tube 130 (e.g., directly after the probe tube 130, directly after the lint trap 226, or the like). In other embodiments of the invention temperature sensors 190 may be located in other areas of the apparatus 100, or more temperature sensors may be utilized in other areas. The temperature sensors 190 may provide information that allows the software to determine if the water, cleaner, and/or disinfectant is heated to the desired temperatures for the cleaning, rinsing, disinfecting, and final rinsing processes. The wet/dry sensors 290 may be located at the inlet to the heating assembly 260, at the inlet to the probe reservoir assembly 120, in the probe reservoir 122, or at the exit of the probe tube 130 (e.g., directly after the probe tube 130, directly after the lint trap 226, or the like). In other embodiments of the invention the wet/dry sensors 290 may be located in other areas of the apparatus 100. The wet/dry sensors 290 may provide information that allows the software to determine if the liquid (e.g., water, cleaner, or disinfectant) is or is not located in the desired areas during different times of the cleaning and disinfecting process. As such, the software may provide information regarding the temperatures, and the locations and duration that the fluids are present within the apparatus 100 to the user through the output device 168 (e.g., printed, displayed in an interface, or the like). Moreover, the software may indicate whether or not the probe passed the cleaning, rinsing, disinfecting, and final rinsing process steps without encountering any errors.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other changes, combinations, omissions, modifications and substitutions, in addition to those set forth in the above paragraphs, are possible. Those skilled in the art will appreciate that various adaptations, modifications, and combinations of the just described embodiments can be configured without departing from the scope and spirit of the invention. Therefore, it is to be understood that, within the scope of the appended claims, the invention may be practiced other than as specifically described herein.

What is claimed is:

1. An apparatus for cleaning and disinfecting probes, the apparatus comprising:
   a probe reservoir, wherein the probe reservoir secures at least a portion of a probe for the cleaning and the disinfecting;
   a fluid circuit operatively coupled to the probe reservoir;
   a heater operatively coupled to the fluid circuit;
   a water inlet operatively coupled the fluid circuit;
   a cleaner assembly comprising:
      a cleaner reservoir having a cleaner; and
      a cleaner dispenser operatively coupled to the cleaner reservoir and the fluid circuit;
   a disinfectant assembly comprising:
      a disinfectant reservoir operatively coupled to the fluid circuit; and a puncture means for puncturing a disinfectant container having only a single concentrated dose of disinfectant; and a main pump operatively coupled to the fluid circuit;

wherein the cleaner assembly is separate from the disinfectant assembly;

wherein the cleaner is dispensed using the cleaner dispenser and mixed with water from the water inlet, heated by the heater and delivered to the probe reservoir by the main pump for cleaning the probe using one or more cleaning cycles; and wherein water from the water inlet is mixed with the single concentrated dose of disinfectant to form a disinfectant, the disinfectant is heated by the heater, and the disinfectant is delivered to the probe reservoir for disinfecting the probe after cleaning using one or more disinfecting cycles.

2. The apparatus of claim 1, further comprising:
a disinfectant release valve operatively coupled to the disinfectant reservoir and the fluid circuit to release the single concentrated dose of disinfectant to the fluid circuit for mixing with the water.

3. The apparatus of claim 1, further comprising:
a fluid release valve operatively coupled to the probe reservoir and the fluid circuit to release the cleaner, the disinfectant, and the water to the probe reservoir.

4. The apparatus of claim 3, further comprising:
a circulating valve operatively coupled to the probe reservoir and the fluid circuit to allow or prevent the cleaner, the disinfectant, and the water to circulate through the probe reservoir and the fluid circuit.

5. The apparatus of claim 1, further comprising:
a water valve operatively coupled to the fluid circuit for turning the water inlet on and off.

6. The apparatus of claim 1, further comprising:
a disinfectant drain valve operatively coupled to the fluid circuit for draining the disinfectant or disinfectant rinse water.

7. The apparatus of claim 6, further comprising:
a cleaner drain valve operatively coupled to the fluid circuit for draining the cleaner or cleaner rinse water.

8. The apparatus of claim 1, further comprising:
a filter operatively coupled to the probe reservoir for removing foreign materials from the cleaner during the one or more cleaning cycles.

9. The apparatus of claim 1, further comprising:
a water filter for filtering the water to 0.2 micron filtered bacteria free water.

10. A method of cleaning and disinfecting probes, the method comprising:
receiving a probe in a probe reservoir such that at least a portion of the probe is located inside of the probe reservoir for the cleaning and the disinfecting;
receiving a single use disinfectant container in a disinfectant reservoir of a disinfectant assembly, wherein the single use disinfectant container has only a single concentrated dose of disinfectant;
cleaning the probe before disinfecting using a cleaner assembly by:
delivering a cleaner from a cleaner reservoir to a fluid circuit using a cleaner dispenser;
mixing the cleaner with water from a water inlet in the fluid circuit;
heating the cleaner; and
delivering the cleaner to the probe in the probe reservoir in one or more cleaner cycles through the use of a main pump and the fluid circuit operatively coupled to the probe reservoir; and disinfecting the probe after cleaning by:
puncturing the single use disinfectant container;
mixing the single concentrated does of disinfectant with water from the water inlet to form a disinfectant;
heating the disinfectant; and
delivering the disinfectant to the probe in the probe reservoir in one or more disinfectant cycles through the use of the pump and the fluid circuit;
wherein the cleaner assembly is separate from the disinfectant assembly.

11. The method of claim 10, wherein the cleaner is heated to a cleaner temperature in a range of 35 degrees Celsius to 45 degrees Celsius, inclusive.

12. The method of claim 10, wherein the cleaner is heated by heating a concentrated cleaner before mixing with the water, heating the cleaner after the concentrated cleaner is mixed with the water, or by heating the water before mixing with the concentrated cleaner.

13. The method of claim 10, wherein cleaning the probe occurs in the one or more cleaning cycles for at least 5 mins.

14. The method of claim 10, wherein the disinfectant is heated to a disinfectant temperature in a range of 38 degrees Celsius to 40 degrees Celsius, inclusive.

15. The method of claim 10, wherein the disinfectant is heated by heating the single concentrated dose of disinfectant before mixing with the water, heating the disinfectant after the single concentrated dose of disinfectant is mixed with water, or by heating the water before mixing with the single concentrated dose of disinfectant.

16. The method of claim 10, wherein disinfecting the probe occurs in one or more disinfectant cycles for at least 5 mins.

17. The method of claim 10, further comprising:
rinsing the probe and the fluid circuit with the water through one or more rising cycles after the cleaning and before the disinfecting; and
rinsing the probe and the fluid circuit with the water through one or more rinsing cycles after the disinfecting;
wherein the water for the one or more rinsing cycles after cleaning or after disinfecting is heated.

18. The method of claim 10, wherein the method of the cleaning and the disinfecting the probe takes less than 25 minutes.

19. The method of claim 10, further comprising:
draining the disinfectant after disinfecting in a disinfect drain line separate from a cleaner drain line for the cleaner.

20. The method claim 10, further comprising:
releasing the single concentrated dose of disinfectant to the fluid circuit for mixing with the water using a disinfectant release valve operatively coupled to the disinfectant reservoir and the fluid circuit;
releasing the cleaner, the disinfectant, and the water to the probe reservoir using a fluid release valve operatively coupled to the probe reservoir and the fluid circuit;
allowing or preventing the cleaner, the disinfectant, and the water to circulate through the probe reservoir and the fluid circuit using a circulating valve operatively coupled to the probe reservoir and the fluid circuit;
turning the water inlet on and off using a water valve operatively coupled to the fluid circuit;
draining the cleaner or cleaner rinse water using a cleaner drain valve operatively coupled to the fluid circuit; and draining the disinfectant or disinfectant rinse water using a disinfectant drain valve operatively coupled to the fluid circuit for draining.

\* \* \* \* \*